United States Patent [19]

Vickery et al.

[11] 4,368,186

[45] Jan. 11, 1983

[54] METHODS AND COMPOSITIONS FOR INTRAVAGINAL CONTRACEPTION

[75] Inventors: Brian H. Vickery, Cupertino; Shabbir Anik; Richard E. Jones, both of Palo Alto, all of Calif.

[73] Assignee: Syntex (U.S.A.) Inc., Palo Alto, Calif.

[21] Appl. No.: 261,411

[22] Filed: May 7, 1981

[51] Int. Cl.³ .................... A61K 31/74; A61K 31/415
[52] U.S. Cl. ................................. 424/78; 424/273 R; 424/319; 424/DIG. 14
[58] Field of Search .............. 424/78, 273 R, DIG. 14

[56] References Cited

U.S. PATENT DOCUMENTS

| | | | |
|---|---|---|---|
| 3,740,421 | 6/1973 | Schmolka | 424/65 |
| 4,188,373 | 2/1980 | Krezanoski | 424/78 |
| 4,247,552 | 1/1981 | Hallesy et al. | 424/250 |
| 4,277,475 | 7/1981 | Vickery | 424/250 |

*Primary Examiner*—Leonard Schenkman
*Attorney, Agent, or Firm*—Annette M. Moore; Tom M. Moran; Alan M. Krubiner

[57] ABSTRACT

A gel formulation, which is inherently spermicidal and which provides an efficient delivery system for spermicidal and other contraceptively effective compounds intravaginally is disclosed. Said formulation is useful in methods of intravaginal contraception.

22 Claims, No Drawings

METHODS AND COMPOSITIONS FOR INTRAVAGINAL CONTRACEPTION

BACKGROUND OF THE INVENTION

After two decades of effort to devise satisfactory contraceptive methods which depend on metabolic control mechanisms (oral contraceptives and progestational inserts) or on intra-uterine mechanical disruption i.e. intra-uterine devices (IUD's); alternative methods which depend on barriers (diaphragms, condoms) and on topical application of spermicides or other contraceptives (intravaginal foams or suppositories) have not become obsolete, and are still in wide use. These methods attract considerable interest due to their safety, freedom from undesirable side effects, and relative accessibility, without the need for a physician's intervention. The present invention relates to compositions for, and methods of, contraception based on topical intravaginal application of spermicides or other antifertility agents which inhibit sperm function.

Present formulations for intravaginal application of sperm function inhibitors are designed to insure coverage of the entire vaginal vault with the active ingredient (usually a surfactant, and typically nonoxynol-9, a non-ionic surfactant).

Thus, while the form of application of the spermicide may be varied, such as, gel, foam, cream, or a suppository designed to disintegrate and spread by means of, for example, an effervescent dissolution process, all of these application methods are basically similar to barrier methods in that they depend in the final analysis, on encountering and destroying all sperm which enter the vagina.

For this reason, the present formulations cannot be considered totally satisfactory solutions to the problem. If they succeed in coverage of the entire vaginal surface, they are inherently messy and unaesthetic. If they fail to do so, they are relatively ineffective; a particular problem with those formulations designed in the form of dissolving suppositories.

Compositions using poloxamers which enhance absorption of drugs by certain mucus membranes have been previously disclosed. See U.S. Pat. Nos. 4,100,271 and 4,188,373. These compositions have been directed toward treatment of eye disorders, and have been designed specifically for application to the surface of the eye. They contain a substantial percentage of a polyoxyethylene—polyoxypropylene block copolymer of average molecular weight 5,000–15,000, a "poloxamer," commonly sold under the trade name Pluronic.

It has now been found that compositions designed for intravaginal application containing poloxamers in substantial amount, have unexpected inherent spermicidal properties, and are uniquely suitable for effective delivery of anti-spermatozoal agents to intercept sperm otherwise destined to penetrate the cervical mucus.

SUMMARY OF THE INVENTION

In one aspect, the invention concerns pharmaceutical compositions designed to effect intravaginal contraception, which consist essentially of
(a) a contraceptively effective amount of a sperm function inhibitor;
(b) between about 10% and 30% by weight of a polyoxyethylene—polyoxypropylene block copolymer, having an average molecular weight between about 5,000 and 15,500; and
(c) water and, optionally, other non-toxic pharmaceutically acceptable excipients.

In a second aspect, the invention concerns a method of contraception which comprises administering the above composition intravaginally prior to coitus.

DETAILED DESCRIPTION

In the context of the present invention, "sperm function inhibitor" refers to compounds which render sperm incapable of fertilizing the female subject, whether by immobilizing, altering, or killing them. These agents are in the general contraceptive class, but are distinguished by directing their effects to the capacity of the sperm to fertilize, rather than altering the metabolism of the female, as is the case with, for example, progestational contraceptives. Examples of such sperm function inhibitors include surfactants such as the widely used nonoxynol-9 which appear to be spermicidal; certain mercuric salts, which also kill sperm, certain 1-substituted imidazoles which are both spermicidal and spermatostatic—i.e. immobilizing; and peptide or other synthetic inhibitors of the sperm proteases which mediate the fertilization of the ovum.

It has been shown that the composition of the present invention, but without the sperm function inhibitor, administered as a placebo in tests for spermicidal activity of specific compounds exhibits spermicidal activity of its own. This effect is at least additive to the contraceptive effect of any specific sperm function inhibitor; and, in certain instances, may be synergistic therewith. This result is surprising, in that none of the optional components of the composition nor the poloxamer are commonly useful as contraceptives.

The composition intended for use in the invention has at least three properties which constitute distinct advantages in its applicability to the method of contraception described herein:

(1) it is inherently spermicidal even without the addition of the specifically sperm inhibiting compounds of (a), supra;

(2) it has penetration and solubilization properties which facilitate the delivery of any additional sperm function inhibitor active ingredient to form critical barrier protection;

(3) it has the proper gel consistency at room temperature and body temperature to facilitate application with standard gel application devices.

The spermicidal properties of the gel alone are clearly advantageous in enhancing the effect of any additional sperm function inhibitor used as an active ingredient. The gel has been shown to immobilize sperm in vitro and to reduce fertilization in vivo.

The ability of the composition to deliver the active ingredient represents a more sophisticated approach to the problem of intravaginal contraception than has previously been disclosed. Clearly it is necessary, to achieve the goal of contraception, to affect only those sperm which actually enter the uterus. Therefore, if the sperm function inhibitor can be concentrated in the area of the cervix, the pathway through which the sperm must enter and if large amounts of agent are soluble therein, the purpose of the method can be achieved, without an excess of material being required.

Use of a suitable applicator to allow proper placement of the gel near the cervix, and the physical properties of the gel itself, effect the proper distribution to enhance the retention of the active ingredient in the appropriate location. The solubilizing properties of the composition also permit sufficient active ingredient to be included in the composition.

The present composition is not dependent for its effectiveness on the use of any particular sperm function inhibitor as active ingredient; however, it is especially useful in carrying those inhibitors which are specific with respect to their sperm affecting properties, as opposed to general mechanical disruption such as exhibited by the now commonly used surfactants. Two classes of such compounds are particularly effective. A class of 1-substituted immidazoles which are disclosed in U.S. Pat. No. 4,247,552 incorporated herein by reference are potent spermicides and/or spermatostats. Illustrative of the classes of 1-substituted imidazoles forming a part of the present invention are those represented by the following general structural formula (as well as pharmaceutically acceptable acid addition salts thereof):

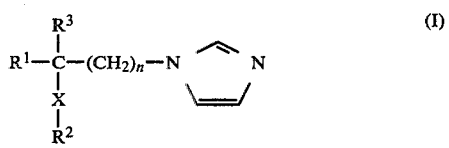

wherein $R^1$ and $R^2$ are each independently alkyl (1–12), alkenyl (1–12), substituted or unsubstituted phenyl or phenyl lower alkyl (1–4), substituted or unsubstituted phenyl lower alkenyl (1–4) wherein "substituted" contemplates substitution by one or more lower alkyl (1–4), halo, lower alkoxy (1–4), trifluoromethyl, nitro or cyano groups;

$R^3$ is hydrogen or lower alkyl (1–4); X is oxygen or sulfur; and n is an integer of from 1 to 4. Within this class, those compounds which bear a branch point in the carbon chain one or two carbons removed from the ring nitrogen of the imidazole are particularly effective. An especially useful group of compounds of this class are those showing the following combination of substituents:

(i) $R^1$ is alkyl, $R^2$ is alkyl, substituted or unsubstituted phenyl, substituted or unsubstituted benzyl, $R^3$ is hydrogen and n is 1 or 2;

(ii) $R^1$ is substituted or unsubstituted phenyl, $R^2$ is substituted or unsubstituted benzyl, $R^3$ is hydrogen and n is 1;

(iii) $R^1$ is substituted or unsubstituted phenethyl, $R^2$ is substituted or unsubstituted phenyl, $R^3$ is hydrogen and n is 1; and (iv) $R^1$ is substituted or unsubstituted benzyl, $R^2$ is substituted or unsubstituted phenyl or benzyl, $R^3$ is hydrogen and n is 2.

One especially preferred group of compounds are those wherein $R^1$ is alkyl having from 3 to 7 carbon atoms, more preferably from 4 to 6 carbon atoms, and most preferably 5 carbon atoms, $R^2$ is substituted or unsubstituted phenyl, preferably phenyl substituted with halo or lower alkyl, and n is 2.

A second especially preferred group of compounds are those wherein $R^1$ is alkyl having from 4 to 8 carbon atoms, $R^2$ is substituted or unsubstituted benzyl and n is 1.

Representative of compounds of formula (I) are the following compounds:

1-[2-(4-chlorobenzylthio)-2-(2,4-dichlorophenyl)ethyl]imidazole nitrate;
1-[2-(2,6-dichlorophenylthio)-4-(4-chlorophenyl)-n-butyl]imidazole nitrate;
1-[2-(2,4-dichlorobenzyloxy)-2-(2,4-dichlorophenyl)ethyl]imidazole nitrate;
1-[2-n-heptylthio-2-(2,4-dichlorophenyl)ethyl]imidazole nitrate;
1-[3-(n-octylthio)octyl]imidazole oxalate;
1-[3-(4-chlorophenylthio)octyl]imidazole oxalate;
1-[2-(4-methoxybenzylthio)-2-(2,4-dichlorophenyl)ethyl]imidazole nitrate;
1-[2-(2,4-dichlorobenzyloxy)-4-(4-chlorophenyl)-n-butyl]imidazole nitrate;
1-[2-(4-chlorobenzyloxy)-2-(2,4-dichlorophenyl)ethyl]imidazole nitrate;
1-(3-n-dodecylthio-n-butyl)imidazole oxalate;
1-[3-(4-chlorobenzylthio)-n-ocytl]imidazole nitrate;
1-(3-n-hexyloxy-n-ocytl)imidazole oxalate;
1-(2-n-octylthio-n-octyl)imidazole oxalate;
1-[3-(4-chlorobenzyloxy)-n-octyl]imidazole oxalate;
1-[3-(2,4-dichlorobenzyloxy)-n-octyl]imidazole oxalate;
1-[2-(4-chlorophenylthio)-4-(4-chlorophenyl)-n-butyl]imidazole nitrate;
1-[3-(2-chlorobenzylthio)-4-(4-chlorophenyl)-n-butyl]imidazole nitrate;
1-[2-(2,4-dichlorobenzyloxy)-n-octyl]imidazole oxalate;
1-[2-(4-chlorobenzylthio)-n-octyl]imidazole nitrate;
1-[3-(2,4-dichlorophenylthio)-n-heptyl]imidazole oxalate;
1-[2-(2,4-dichlorophenylthio)-2-methyl-n-hexyl]imidazole nitrate;
1-(2-ethylthiotetradecyl)imidazole oxalate;
1-[3-(4-chlorophenylthio)-3-(2,4-dichlorophenyl)-n-propyl]imidazole;
1-[4-(4-chlorophenylthio)-4-(2,4-dichlorophenyl)-n-butyl]imidazole oxalate;
1-[3-(4-tert-butylphenylthio)-n-octyl]imidazole oxalate;
1-[4-(4-chlorobenzyloxy)-4-(2,4-dichlorophenyl)-n-butyl]imidazole nitrate;
1-[3-(n-hexylthio)-3-(2,4-dichlorophenyl)-n-propyl]imidazole oxalate; and
1-[4-(2,4-dichlorobenzyloxy)-4-(4-chlorophenyl)-n-butyl]imidazole nitrate.

In addition, a number of inhibitors directed against the sperm carried fertilization effector system i.e., acrosyn inhibitors, are described by Bhattacharyya, et al; J. Repro Fertil. 47: 97 (1976) and Yang, et al; Fertil. and Steril 27: 557 (1976). These include, for example, soybean trypsin inhibitors, and synthetics such as tosyl-lysyl-chloromethyl ketone (TLCK).

The gelling and solubilizing properties of the present invention are maintained by using a polyoxyethylene—polyoxypropylene block copolymer of appropriate average molecular weight, optionally along with such additional materials as, for example, polyethylene glycol (PEG) 400. By a suitable amount of the poloxamer, the composition remains gelled at both room temperature of about 15° to about 25° (at which it must be administered) and at a body temperature of approximately 37° C., at which it must maintain its integrity.

In the practice of the invention, the polyoxyethylene—polyoxypropylene block copolymer is of an average molecular weight of approximately between 5000 and 15,500 preferably about 10,000 to 12,000, and constitutes between about 10% and 30% by weight of the composition, preferably 15% to 20%. In a preferred embodiment, the additional excipient polyethylene glycol or similar component constitutes between about 10% and 30% of the composition more preferably between about 15% and 25%.

The poloxamer itself, is formed by condensation of propylene oxide onto a propylene glycol nucleus followed by the condensation of ethylene oxide onto both ends of the polyoxypropylene base. The polyoxyethylene hydrophilic groups on the ends of the molecule are controlled in length to constitute between 10% to 80% of the final molecule. The poloxamer series of products may be represented empirically by the formula:

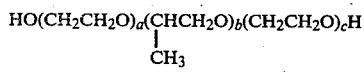

$$HO(CH_2CH_2O)_a(CHCH_2O)_b(CH_2CH_2O)_cH$$
$$|$$
$$CH_3$$

wherein a and c are statistically equal. They have been commercially available in average molecular weights of from about 1100 to 15,500, under the trade-name Pluronic.

In addition to the critical amounts of polyoxyethylene—polyoxypropylene block copolymer, and, preferably of additional polyethylene glycol of similar hydrophilic oligomers, additional pharmaceutical excipients are desirable in the composition. A suitable lower alkylene glycol, such as, for example, glycerin, is a desirable component in order to obtain the appropriate viscosity for the resulting gel. This glycol or glycerol should be present in about 5% to 30% by weight or preferably from about 15% to 25% by weight.

It may also be desirable to buffer the present composition so as to enhance its inherent spermicidal activity. Any suitable compatable buffer solution may be used, that is, weak acids and weak bases and their corresponding salts, to adjust to the desired pH. A useful buffer system for the present invention is the citric acid/citrate system which can be adjusted to an acidic pH to enhance a spermicidal effect. The total percentage of buffering components, should be in the range of 0.5% to 2% of the total composition. Suitable pH ranges are approximately 3 to 6, preferably 4.5 to 5.

Small amounts of antimicrobial preservatives such as parabens, benzyl alcohol and others, and antioxidants such as BHA, BHT and others may also be included to preserve integrity of the preparation during storage.

The percentage of these preservatives should be in the range of 0.01 to 2%, preferably 0.5 to 1%. A small percentage of emulsifying agent is also desirable, to aid stability of the composition. A suitable stabilizing agent is a surfactant such as polysorbate or other nonionic surfactant.

The method of the invention as practiced, of course, depends on the particular circumstances of the subject, and upon the nature of the active ingredient chosen as the sperm function inhibitor. Generally, the administration of the composition containing the active ingredient should take place between about 8 hours to about 2 minutes prior to sexual intercourse. There appears to be no preferable range within this time frame, and therefore, the convenience of the subject is the paramount consideration. The amount of composition to be applied, also varies with the concentration of the active ingredient, and the design of the applicator. An effective amount is between 0.5–6 ml of the gel for human subjects, with correspondingly larger or smaller amounts for other mammals. Preferably, it is desirable from an aesthetic standpoint for human subjects to use a minimum amount of composition, preferably 0.5 to 2 ml total volume, which is facilitated by the accuracy of positioning of the application. If the applicator is so designed that the composition can be deposited approximately at the location of the cervix, which is, of course, the critical surface, a minimal amount of material can be used.

PREFERRED EMBODIMENTS

Preferred forms of the composition are those wherein the polyoxyethylene—polyoxypropylene block copolymer constitutes between 15 and 20% by weight of the final gel composition, and has a molecular weight of approximately 10,000 to 12,000. Still more preferred are those compositions wherein the gel, which contains the above poloxamer, also contains 10% to 30% by weight of polyethylene glycol of the average molecular weight 400. Still more desirable among the above listed preferred embodiments are those wherein, in addition to the previously stated specifications, about 10% to 30% by weight of a lower alkylene glycol, preferably glycerol, is added as a viscosity-controlling agent, and appropriate preservatives and buffers are added to the system.

Preferred active ingredients are selected 1-substituted imidazoles and selected peptide protease inhibitors.

The following examples illustrate the composition and method of the invention. They are intended to be explanatory of its nature and are not to be considered limiting.

EXAMPLE 1

THE PHARMACEUTICAL COMPOSITION OF THIS INVENTION IS EXEMPLIFIED BY THE FOLLOWING COMPOSITION:

| | Percent by wt/vol. |
|---|---|
| Active Ingredient | 1 |
| Poloxamer-407-(Pluronic F-127) | |
| (MW 11,500) | 18 |
| PEG 400 | 20 |
| Glycerin | 20 |
| Polysorbate 60 | 3 |
| BHA | .02 |

-continued

| | Percent by wt/vol. |
|---|---|
| Water, qs ad | 100 |

The composition is prepared by mixing all the ingredients with approximately 90% of the required water and allowing the polyoxyethylene—polyoxypropylene block copolymer to hydrate and completely dissolve with gentle stirring. When a clear gel is obtained, the remaining water is added to adjust the volume to 100 ml. The active ingredient is (±)-1-[2-cyclohexylmethyl)hexyl]imidazole.$H_2SO_4$).

EXAMPLE 2
IN VITRO SPERMICIDAL ACTIVITY OF GEL CONTAINING NO ACTIVE INGREDIENTS:

A gel prepared according to the recipe given in Example 1, but without active ingredient, either undiluted, or diluted in physiological saline as shown in the table below was mixed with an equal volume of rabbit semen. The mixtures were immediately examined under a microscope; the percent of motile sperm was determined visually, and forward progression rated on a scale of 0–4, 4 representing the most motile in directed motion.

| % of Gel in dilution | Spermatozoa | |
|---|---|---|
| | (%) Motile | Forward progession |
| 100 | 0 | 0 |
| 50 | 40, 50 | 1, 2 |
| 25 | 90 | 3 |
| 10 | 90, 90 | 3, 3 |
| 1 | 90 | 3 |
| 0 | 99 | 4 |

A similar determination was carried out using mouse epididymal sperm; with the following results:

| % of Gel in dilution | Spermatozoa | |
|---|---|---|
| | (%) Motile | Forward progession |
| 100 | 0 | 0 |
| 50 | 0, 0 | 0, 0 |
| 25 | 0 | 0 |
| 10 | 0, 10 | 0, 1 |
| 1 | 80 | 3 |
| 0 | 90 | 3 |

EXAMPLE 3
EFFECT ON FERTILIZATION IN THE ARTIFICALLY INSEMINATED RABBIT:

New Zealand white rabbits were superovulated by administration of 150 IU of pregnant mare serum gonadotropin 96 hours before induction of ovulation with 250 IU of human chorionic gonadotropin. At the time of HCG injection, 2 ml of the test sample was inserted intravaginally as deeply as possible. The rabbits were then artificially inseminated with 0.5 ml of semen which had been collected by use of an artificial vagina, and which semen contained at least 80% motile sperm with a motility rating of 4 (see Example 2). The eggs were collected 30 hours after HCG administration and assayed for fertilization.

| Treatment | No. of Animals | No. of Eggs Recovered | Fertilization Rate |
|---|---|---|---|
| 2.0 ml K-Y Jelly | 3 | 106 | 90% |
| 2.0 ml Delfen Foam (12.5%) | 8 | 185 | 15% |
| 2.0 ml gel from Example 1, without active ingredient | 4 | 137 | 35% |
| 2.0 ml gel from Example 1 | 4 | 95 | 0% |

EXAMPLE 4
DELIVERY OF ANTI-SPERMATOZOAL AGENTS BY THE COMPOSITION PROTOCOL:

Stumptail Macaque monkeys were used as experimental subjects. The gel formulations were applied to the vagina using standard gel application techniques two minutes before coitus. After coitus occurred, the vaginal fluids were recovered immediately, and cervical mucus recovered within 15 minutes. The vaginal fluids and mucus were examined for sperm motility. The results, as shown below, indicate that 0% motility of sperm was obtained in both the vaginal fluids and the cervical mucus using the composition of the invention. Results:

| | Number Animals | % of total sperm motile | |
|---|---|---|---|
| | | Vaginal | Cervical Mucus |
| 5% nonoxynol* | 5 | 27% | 39% |
| control | 3 | 82% | 85% |
| composition prepared as in Example 1, | 4 | 0% | 0% |

*commercial preparation; does not include gel of the present invention

What is claimed:

1. A contraceptive gel composition for intravaginal application, which consists essentially of:
    (a) a contraceptively effective amount of a sperm function inhibitor;
    (b) between about 10% and 30% by weight of a polyoxyethylene—polyoxypropylene block copolymer, having an average molecular weight between about 5,000 and 15,500; and
    (c) water, and, optionally, other non-toxic pharmaceutically acceptable excipients.

2. The composition of claim 1 wherein the polyoxyethylene—polyoxypropylene block copolymer in (b) is between 15% and 20% by weight of the gel.

3. The composition of claim 2 wherein the polyoxyethylene—polyoxypropylene block copolymer in (b) has an average molecular weight between about 10,000 and 12,000.

4. The composition of claim 1 wherein the other non-toxic pharmaceutically acceptable excipients in (c) include about 10% to 30% by weight of polyethylene glycol of average molecular weight 400 and about 10% to 30% by weight of lower alkylene glycol.

5. The composition of claim 3 wherein the other non-toxic pharmaceutically acceptable excipients in (c) include about 10% to 30% by weight of polyethylene glycol of average molecular weight 400 and about 10% to 30% by weight of lower alkylene glycol.

6. The composition of claim 1 wherein the sperm function inhibitor in (a) is a 1-substituted imidazole.

7. The composition of claim 1 wherein the sperm function in (a) is an acrosyn inhibitor.

8. The composition of claim 6 wherein the sperm function inhibitor in (a) is about 0.01–1% wt/volume of the composition.

9. The composition of claim 3 wherein the sperm function inhibitor in (a) is a 1-substituted imidazole.

10. The composition of claim 3 wherein the sperm function inhibitor in (a) is an acrosyn inhibitor.

11. The composition of claim 9 wherein the sperm function inhibitor in (a) is about 0.01–1% wt/volume of the composition.

12. A contraceptive gel composition for intravaginal application which consists essentially of
(a) between about 0.01% and 1% of a 1-substituted imidazole, as a sperm function inhibitor;
(b) between about 15% and 20% by weight of polyoxyethylene—polyoxypropylene block copolymer having an average molecular weight between about 10,000 and 12,000; and
(c) between about 10% and 30% by weight of polyethylene glycol of average molecular weight 400 and between about 10% and 30% of glycerin, water, and optionally non-toxic pharmaceutically acceptable excipients.

13. A method of contraception in human beings which method comprises administering, intravaginally, prior to coitus, to a female subject in need of, or desirous of, protection against conception, between about 0.5 ml and 6 ml of a gel composition which consists essentially of
(a) a contraceptively effective amount of a sperm function inhibitor;
(b) between about 10% and 30% by weight of a polyoxyethylene—polyoxypropylene block copolymer, having an average molecular weight between about 5,000 and 15,500; and
(c) water, and, optionally, other non-toxic pharmaceutically acceptable excipients.

14. The method of claim 13 wherein the amount of composition administered is between about 0.5 ml and 2 ml.

15. The method of claim 13 wherein the composition is administered between about 8 hours and 2 minutes prior to coitus.

16. The method of claim 14 wherein the composition is administered between about 8 hours and 2 minutes prior to coitus.

17. The composition of claim 9 wherein the 1-substituted imidazole in (a) is of the formula

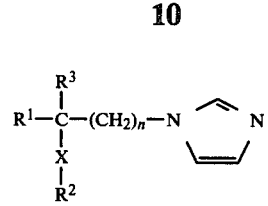

or a pharmaceutically acceptable salt thereof, wherein
$R^1$ and $R^2$ are each independently alkyl (1–12), alkenyl (2–12), phenyl, phenyl lower alkyl (1–4), or phenyl lower alkenyl (2–4) wherein each phenyl ring is optionally substituted by one or more lower alkyl (1–4), halo, lower alkoxy (1–4), trifluoromethyl, nitro or cyano groups;
$R^3$ is hydrogen or lower alkyl (1–4);
X is oxygen or sulfur; and
n is an integer of from 1 to 4.

18. The composition of claim 17 wherein $R^1$ is alkyl of four to eight carbon atoms; $R^2$ is benzyl optionally substituted by one or more lower alkyl (1–4), halo, lower alkoxy (1–4), trifluoromethyl, nitro or cyano; $R^3$ is hydrogen or lower alkyl (1–4); X is oxygen or sulfur; and n is 1; or a pharmaceutically acceptable acid addition salt thereof.

19. The composition of claim 18 wherein $R^1$ is n-hexyl, $R^2$ is 2,4-dichlorobenzyl, $R^3$ is hydrogen, X is oxygen and n is 1, namely, 1-[2-(2,4-dichlorobenzyloxy)-n-octyl]imidazole or a pharmaceutically acceptable acid addition salt thereof.

20. The composition of claim 12 wherein the 1-substituted imidazole in (a) is of the formula

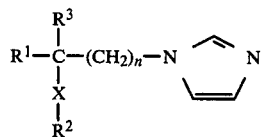

or pharmaceutically acceptable salt thereof, wherein
$R^1$ and $R^2$ are each independently alkyl (1–12), alkenyl (2–12), phenyl, phenyl lower alkyl (1–4), or phenyl lower alkenyl (2–4) wherein each phenyl ring is optionally substituted by one or more lower alkyl (1–4), halo, lower alkoxy (1–4), trifluoromethyl, nitro or cyano groups;
$R^3$ is hydrogen or lower alkyl (1–4);
X is oxygen or sulfur; and
n is an integer of from 1 to 4.

21. The composition of claim 20 wherein $R^1$ is alkyl of four to eight carbon atoms; $R^2$ is benzyl optionally substituted by one or more lower alkyl (1–4), halo, lower alkoxy (1–4), trifluoromethyl, nitro or cyano; $R^3$ is hydrogen or lower alkyl (1–4); X is oxygen or sulfur and n is 1; or a pharmaceutically acceptable acid addition salt thereof.

22. The composition of claim 21 wherein $R^1$ is n-hexyl, $R^2$ is 2,4-dichlorobenzyl, $R^3$ is hydrogen, X is oxygen and n is 1, namely, 1-[2-(2,4-dichlorobenzyloxy)-n-octyl]imidazole or a pharmaceutically acceptable acid addition salt thereof.

* * * * *